US00PP17988P3

(12) United States Plant Patent
Jandrew

(10) Patent No.: US PP17,988 P3
(45) Date of Patent: Sep. 4, 2007

(54) ***PENSTEMON* PLANT NAMED 'PHENI REEDA'**

(50) Latin Name: ***Penstemon hartwegii* Benth**
Varietal Denomination: Pheni Reeda

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 15 days.

(21) Appl. No.: 11/301,566

(22) Filed: Dec. 13, 2005

(65) Prior Publication Data

US 2007/0136913 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer

(74) *Attorney, Agent, or Firm*—Jondle & Associates P.C.

(57) ABSTRACT

A new *Penstemon* plant particularly distinguished by brilliant red and white flowers, medium size inflorescences, early flowering, medium-green foliage with narrow lanceolate leaves, medium vigorous growth, and an upright plant habit that is well-branched with steady and sturdy stems is disclosed.

2 Drawing Sheets

Genus and species: *Penstemon hartwegii* Benth.
Variety denomination: 'Pheni Reeda'.

BACKGROUND OF THE NEW PLANT

The present invention comprises a new and distinct cultivar of *Penstemon,* botanically known as *Penstemon hartwegii,* and hereinafter referred to by the cultivar name 'Pheni Reeda'. The new cultivar originated from a hybridization made in 2002 in Gilroy, Calif. The female parent is a proprietary *Penstemon* plant designated '106-1' (unpatented) having dark pink flowers, and the male parent is a proprietary *Penstemon* plant designated '109-2' (unpatented) having red flowers. The seeds produced by the hybridization were sown in November 2002, and the resulting seedlings were selected in May 2003. A single plant selection was chosen for further evaluation and for asexual propagation in the summer of 2003.

The new cultivar was created in 2002 in Gilroy, Calif. and has been asexually reproduced repeatedly by vegetative cuttings and tissue culture in Gilroy, Calif. over a three-year period. The plant has also been trialed at Gilroy, Calif., and Hillscheid, Germany. The present invention has been found to retain its distinctive characteristics through successive asexual propagations.

Plant Breeder's Rights for this cultivar were applied for in Europe on Oct. 14, 2005 and in Canada on Mar. 29, 2005.

SUMMARY OF THE INVENTION

The following are the most outstanding and distinguishing characteristics of this new cultivar when grown under normal horticultural practices in Gilroy, Calif. and Hillscheid, Germany.

1. Brilliant red and white flowers;
2. Medium sized inflorescences;

3. Early flowering;
4. Medium green foliage with narrow lanceolate leaves;
5. Medium vigorous growth; and
6. An upright and well-branched plant habit with steady and sturdy stems.

DESCRIPTION OF PHOTOGRAPHS

This new *Penstemon* plant is illustrated by the accompanying photographs which show blooms, buds, and foliage of the plant in full color; the colors shown are as true as can be reasonably obtained by conventional photographic procedures. The photographs are of whole plants about 3 months old, grown in a field in Gilroy, Calif. in mid July 2005.

DESCRIPTION OF THE NEW CULTIVAR

Figure 1:
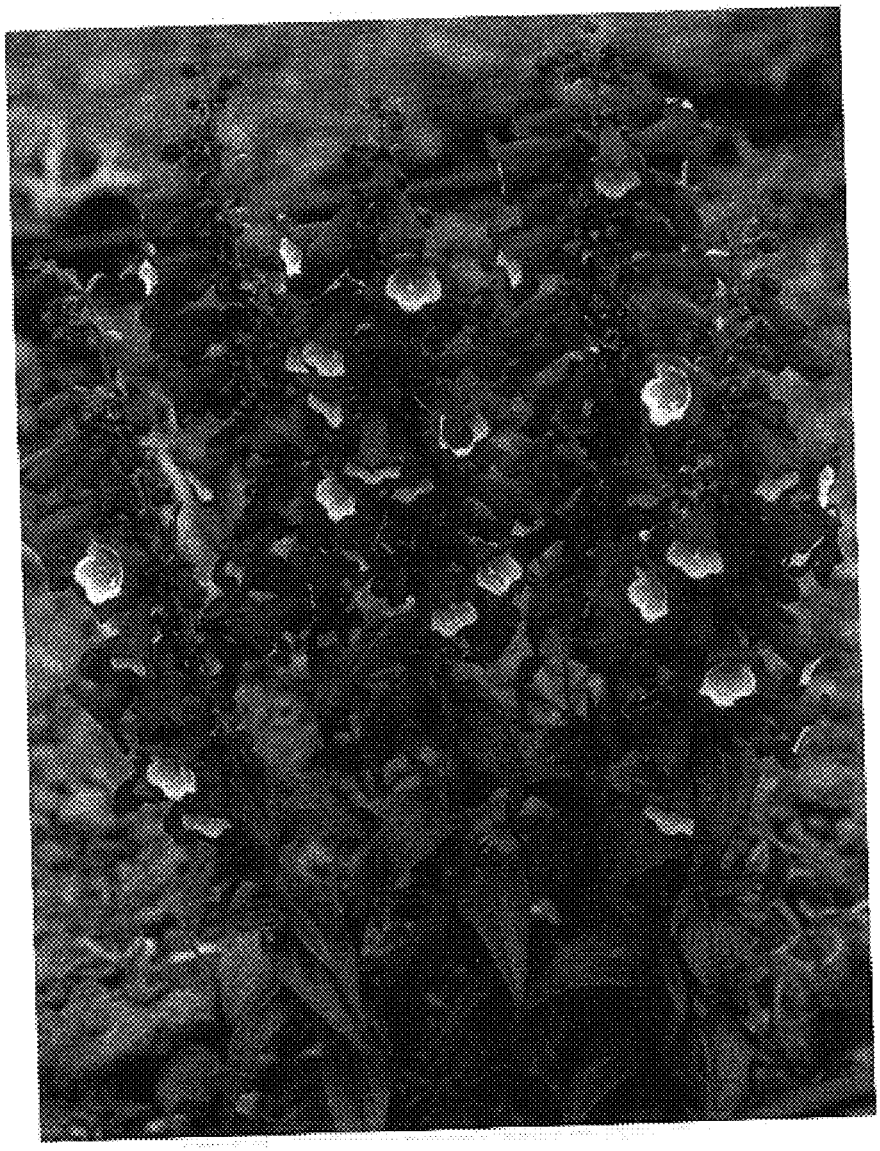
FIG. 1 shows the overall plant habit, including blooms, buds, mature foliage, and plant habit.
Figure 2:
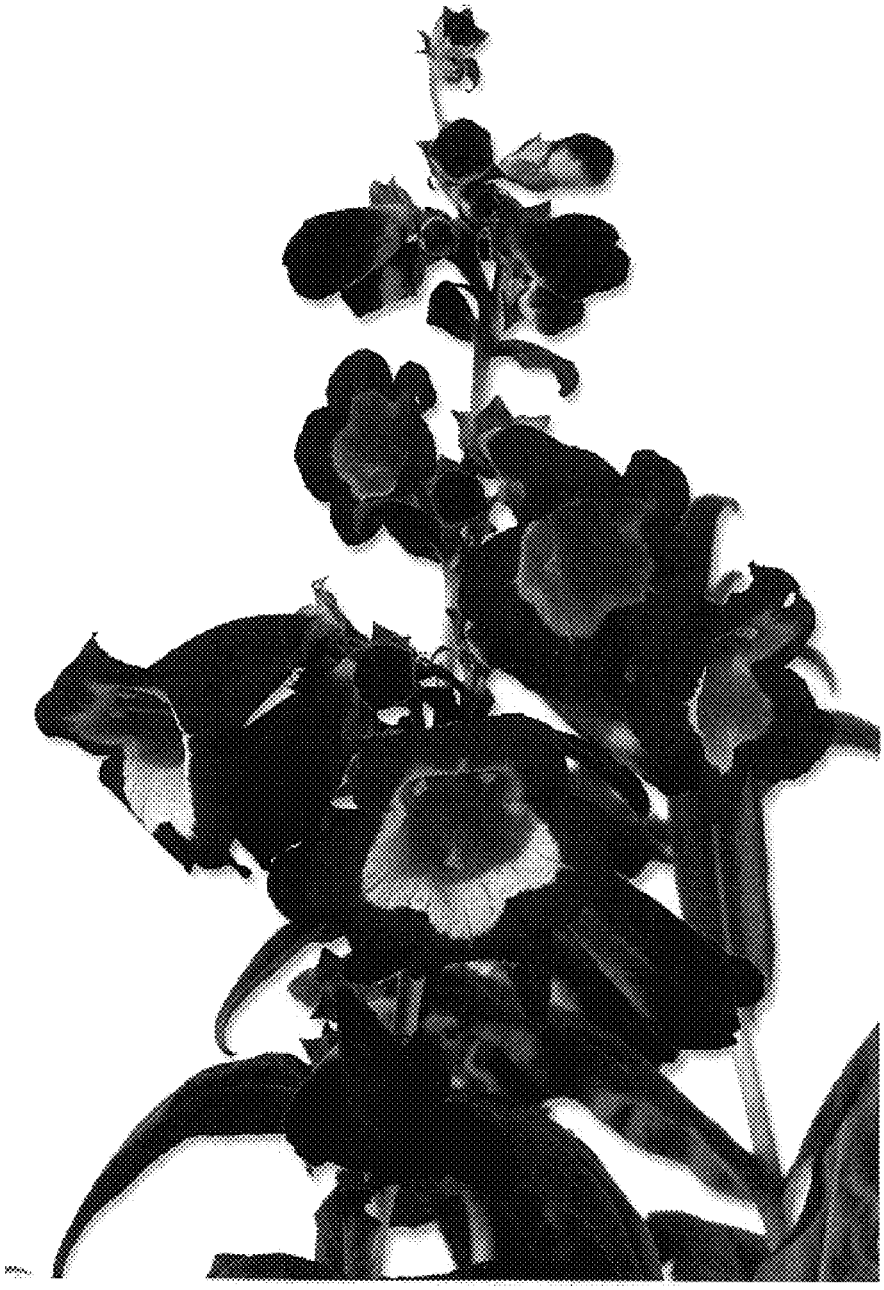
FIG. 2 shows a close-up of the mature inflorescences.

The following detailed descriptions set forth the distinctive characteristics of 'Pheni Reeda'. The data which define these characteristics were collected from asexual reproductions carried out in Gilroy, Calif. The plant history was taken on nine-to eleven-week-old plants grown in Hillscheid, Germany in 2005. Rooted cuttings were planted into 12-cm plastic pots placed in a greenhouse. The plants were not pinched, so they mostly developed into single-stem plant habits. Most observations were made after nine weeks at the beginning of flowering. Color readings were taken under natural light. Color references are primarily to the R.H.S. Colour Chart of The Royal Horticultural Society of London (R.H.S.) (2001 edition).

DETAILED BOTANICAL DESCRIPTION OF THE NEW PLANT

Classification:

*Family.*—Scrophulariaceae.

*Botanical name.*—*Penstemon hartwegii* Benth.

Parentage:

*Female parent.*—'106-1' a proprietary dark pink-flowered *Penstemon* plant (unpatented).

*Male parent.*—'109-2' a proprietary red-flowered *Penstemon* plant (unpatented).

Growth:

*Form.*—Herbaceous perennial; suffrutescent; tolerates only slight frost; usually cultivated as an annual plant.

*Habit.*—Un-pinched plants develop one flowering stem with no secondary branches at the base; for commercial purposes, the plants are usually pinched so that 5–10 stems of equal height will develop.

*Height.*—69 cm for a 9-week-old single-stem plant in late summer.

*Width.*—About 15 cm.

*Time to produce a finished flowering plant.*—10 weeks for a single-stem plant in a 5-inch pot (spring cultivation); about 12–13 weeks for a branched plant.

*Outdoor plant performance.*—Use in garden beds or in container planting.

*Time to initiate and develop roots.*—21 days in the spring.

*Root description.*—Somewhat fleshy at the base, mainly fibrous, and self-branching.

Leaves:

*Arrangement.*—Opposite and decussate.

*Shape.*—Lanceolate.

*Apex.*—Acute.

*Base.*—Sessile.

*Margin.*—Very weakly crenate with fine, short bristles.

*Immature.*—Color: Upper surface: RHS 143B. Lower surface: RHS 143C. Texture: Very finely pubescent.

*Mature* (*fully expanded*).—Length: 10.5 cm. Width: 3.5 cm. Color: Upper surface: RHS 137D (medium green). Lower surface: Between RHS 138A and RHS 138B. Texture: Smooth, glabrous, and slightly glossy.

*Venation.*—Type: Pinnate. Color: RHS 145C on the lower side; venation hardly visible on the upper surface.

Stems:

*Length.*—45 cm, without inflorescence, as measured from the base upward (to the tip), excluding the inflorescence.

*Diameter.*—0.5 cm as measured at the midpoint.

*Internode length.*—4–5 cm.

*Color.*—RHS 144B.

*Texture.*—Sparse with fine pubescence.

*Anthocyanin.*—RHS 174B (brown), weakly present at the base of the secondary branches.

Flower bud:

*Shape.*—Tube-shaped with a closed end.

*Diameter.*—1.3 cm.

*Length.*—3.5 cm.

*Color* (*at tight bud*).—From RHS 45B at the tip to RHS 45C near the base.

Inflorescence:

*Inflorescence type.*—A terminal raceme, or rather thyrse with two short secondary penduncles at every node, each peduncle bearing 4 to 5 flowers or buds at different stages of development.

*Blooming habit.*—Intermittent; removing of spent flowers enhances development of new flowers.

*Quantity of inflorescence per plant.*—One (for a single stem plant).

*Lastingness of individual blooms on the plant.*—4 to 5 days.

*Fragrance.*—None.

*Inflorescence length.*—24 cm (approximately one-third of the total height).

*Inflorescence width.*—Up to 12 cm.

*Penduncle.*—Color: RHS 144B (light green). Length: Up to 4 cm. Diameter: 0.2 cm–0.3 cm.

Flower:

*Type.*—Funnel-shaped with petals mainly fused, 5-lobed with the free lobes opened outward or somewhat reflexed.

*Floret quantity* (*per raceme*).—Approximately 30 to 35.

*Shape.*—Funnel-shaped.

*Floret diameter.*—3.8 cm at the free end.

*Floret length* (*or depth*).—4.2 cm.

*Color.*—General: Bright red. Petal lobes and outer surface of corolla: RHS 46C. Corolla (inner surface): RHS N155B.

*Petals* (*lobes*).—Quantity: 5. Arrangement: Two upper lobes with two lateral lobes and one lower lobe. Apex: Rounded. Base: Fused and funnel-shaped. Margin: Entire. Texture: Smooth.

*Upper lobes, size.*—Length (from the Corolla opening): 1.0 cm. Width: 1.3 cm.

*Lateral lobes, size.*—Length (from the Corolla opening): 1.0 cm. Width: 1.4 cm.

*Lower lobe.*—Length (from the Corolla opening): 0.9 cm. Width: 1.2 cm.

*Sepals.*—Quantity: 5, in an overlapping arrangement. Color: RHS 143C (both surfaces green). Length: 0.7 to 0.8 cm. Width: 0.6 cm. Shape: Ovate. Apex: Acute and somewhat crenate at the tip. Base: Attenuate. Anthocyanin: RHS 185C (purple-pink) at the lateral margins. Texture: Finely pubescent.

*Pedicels.*—Color: RHS 144A (near the flower base anthocyanin may occur, RHS 184A). Length: 0.5 cm to 0.7 cm. Diameter: 0.1 cm to 0.2 cm. Texture: Pubescent (covered with very short hair).

Reproductive organs:

*Stamens.*—Quantity: 5 total, of which 4 are fertile. Filament: Color: RHS 155D (white). Length: Two are 2.5 cm and two are 3.2 cm. Diameter: 0.1 cm. Anther color: Approximately RHS 187D (grey-violet). Pollen amount: Abundant. Pollen color: RHS 4D (pale yellow).

*Pistils.*—Quantity: 1. Length: 2.8 to 3.2 cm. Stigma color: RHS 155A (white). Style color: Lower part: RHS N74D (violet-pink). Upper part: RHS 155D (white).

Fruit and seed set: Plants are fertile; frequently, an ovate capsule with a threadlike pistil initially visible; ovary is ovate, 0.5 cm in length and 0.3–0.4 cm in diameter; when the corolla drops, the ovary develops into a seed capsule (ovate) of about 1.0 cm in length and 0.6 cm in diameter.

*Seed.*—Color: RHS 200B. Shape: Irregularly round (a few more oblong), wrinkled and pitted. Diameter: 0.15 cm.

Disease and insect resistance: Has not been observed.

COMPARISON WITH PARENTAL AND COMMERCIAL CULTIVARS

'Pheni Reeda' differs from the female parent, proprietary *Penstemon* plant '106-1' (unpatented), in that 'Pheni Reeda' has bright red flowers, while '106-1' has dark pink flowers. Additionally, 'Pheni Reeda' has darker green leaves, and is earlier to flower than '106-1'.

'Pheni Reeda' differs from the male parent, proprietary *Penstemon* plant '109-2' (unpatented), in that 'Pheni Reeda' has a deeper red flower color than the red flower color of '109-2'. Additionally, 'Pheni Reeda' has stronger branching ability '109-2'.

'Pheni Reeda' differs from the commercial cultivar 'Cathedral Hot Rose' (patent status unknown) in that 'Pheni Reeda' has a main flower color of red, while the main flower color of 'Cathedral Hot Rose' is magenta. Additionally, 'Pheni Reeda' has a more compact plant habit and flowers earlier than 'Cathedral Hot Rose'.

I claim:

1. A new and distinct cultivar of *Penstemon* plant as shown and described herein.

* * * * *